US009682898B2

United States Patent
Peitz et al.

(10) Patent No.: US 9,682,898 B2
(45) Date of Patent: Jun. 20, 2017

(54) OLIGOMERIZATION OF C4 STREAMS WITH VERY LOW 1 BUTENE CONTENT

(71) Applicants: Stephan Peitz, Oer-Erkenschwick (DE); Frank Geilen, Haltern am See (DE); Dietrich Maschmeyer, Recklinghausen (DE); Guido Stochniol, Haltern am See (DE)

(72) Inventors: Stephan Peitz, Oer-Erkenschwick (DE); Frank Geilen, Haltern am See (DE); Dietrich Maschmeyer, Recklinghausen (DE); Guido Stochniol, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/901,177

(22) PCT Filed: Jun. 25, 2014

(86) PCT No.: PCT/EP2014/063374
§ 371 (c)(1),
(2) Date: Dec. 28, 2015

(87) PCT Pub. No.: WO2014/207034
PCT Pub. Date: Dec. 31, 2014

(65) Prior Publication Data
US 2016/0152527 A1    Jun. 2, 2016

(30) Foreign Application Priority Data
Jun. 27, 2013   (DE) ........................ 10 2013 212 481

(51) Int. Cl.
| | | |
|---|---|---|
| C07C 2/08 | (2006.01) | |
| C07C 2/10 | (2006.01) | |
| C10G 50/00 | (2006.01) | |
| C07C 4/02 | (2006.01) | |
| C07C 5/03 | (2006.01) | |
| C07C 5/48 | (2006.01) | |
| C07C 29/04 | (2006.01) | |
| C07C 41/06 | (2006.01) | |
| C07C 45/50 | (2006.01) | |
| C07D 305/10 | (2006.01) | |

(52) U.S. Cl.
CPC ............... *C07C 2/08* (2013.01); *C07C 2/10* (2013.01); *C07C 4/02* (2013.01); *C07C 5/03* (2013.01); *C07C 5/48* (2013.01); *C07C 29/04* (2013.01); *C07C 41/06* (2013.01); *C07C 45/505* (2013.01); *C07D 305/10* (2013.01); *C10G 50/00* (2013.01); *C07C 2521/04* (2013.01); *C07C 2521/08* (2013.01); *C07C 2521/12* (2013.01); *C07C 2523/755* (2013.01); *C07C 2529/76* (2013.01); *C10G 2300/1092* (2013.01); *C10G 2400/02* (2013.01); *C10G 2400/22* (2013.01)

(58) Field of Classification Search
CPC ....................................................... C07C 2/08
USPC ....................................................... 549/464
See application file for complete search history.

(56) References Cited

U.S. PATENT DOCUMENTS

| | | | |
|---|---|---|---|
| 6,846,965 B1 | 1/2005 | Schulz et al. | |
| 6,852,898 B2 * | 2/2005 | Schulz ................ | B01J 19/2465 585/530 |
| 7,291,759 B2 | 11/2007 | Heidemann et al. | |
| 9,200,216 B2 | 12/2015 | Boeing et al. | |
| 2004/0181105 A1 | 9/2004 | Heidemann et al. | |
| 2013/0131416 A1 | 5/2013 | Crone et al. | |
| 2015/0336861 A1 | 11/2015 | Geilen et al. | |

FOREIGN PATENT DOCUMENTS

WO    WO 99/25668 A1    5/1999

OTHER PUBLICATIONS

International Search Report issued Aug. 26, 2014 in PCT/EP2014/063374.

* cited by examiner

*Primary Examiner* — Taofiq A Solola
(74) *Attorney, Agent, or Firm* — Oblon, McClelland, Maier & Neustadt, L.L.P.

(57) ABSTRACT

An OCTOL process is disclosed which by limitation of the conversion in its individual oligomerization steps is set up particularly for the productive utilization of $C_4$ feedstock mixtures with a low 1-butene content and which nevertheless yields a $C_8$ product mixture having an Iso index suitable for the preparation of plasticizer alcohols.

15 Claims, 4 Drawing Sheets

OLIGOMERIZATION OF C4 STREAMS WITH VERY LOW 1 BUTENE CONTENT

The present invention relates to a process according to the pre-characterizing clause of Claim 1. A process of this kind is called an OCTOL process.

Oligomerization is understood to be the reaction of hydrocarbons with themselves, forming correspondingly longer-chain hydrocarbons. Particularly amenable to oligomerization are olefins (i.e. alkenes), these being aliphatic hydrocarbons which possess at least one carbon double bond in the molecule. Accordingly, for example, by the oligomerization of two olefins having three carbon atoms (dimerization), it is possible to synthesize an olefin having six carbon atoms. If, instead, three olefins having three carbon atoms joined together (trimerization), the product is an olefin having nine carbon atoms. Where butenes—these being olefins having four carbon atoms—are subjected to oligomerization, the products include substantially olefins having eight carbon atoms (hereinafter $C_8$ olefins, otherwise often also called "dibutenes"), olefins having twelve carbon atoms ($C_{12}$ olefins, "tributenes") and also, to a smaller extent, olefins having more than twelve carbon atoms ($C_{12+}$ olefins).

The invention is concerned exclusively with the oligomerization of $C_4$ olefins, producing predominantly, by dimerization and trimerization, $C_8$ and $C_{12}$ olefins.

The $C_4$ olefins include the four isomeric compounds 1-butene, cis-2-butene, trans-2-butene and isobutene. 1-Butene and the two 2-butenes belong to the group of the linear butenes, while isobutene represents a branched olefin. The linear $C_4$ olefins 1-butene, cis-2-butene and trans-2-butene are also grouped together as "n-butenes".

A contemporary overview of the chemical and physical properties of the butenes and also of their technical processing and productive utilization is offered by the following publication:

F. Geilen, G. Stochniol, S. Peitz and E. Schulte-Koerner: Butenes. Ullmann's Encyclopedia of Industrial Chemistry. (2013)

Butenes are formed in the cracking of petroleum fractions in a steamcracker or in a fluid-catalytic cracker (FCC). In this case, however, the butenes are obtained not in pure form but instead as what is called a "$C_4$ cut". This is a mixture of hydrocarbons having four carbon atoms, the composition of this mixture differing according to provenance, this mixture including not only $C_4$ olefins but also saturated $C_4$ hydrocarbons (alkanes). Additionally there may be traces of hydrocarbons having more or less than four carbon atoms (for example, but not exclusively, propane and/or pentenes), and other organic or inorganic constituents. Butenes are sourced alternatively from, for example, chemical processes, such as the dehydrogenation of butanes, and also the fermentative or pyrolytic conversion of renewable raw materials.

Alkanes are hydrocarbons in which the carbon atoms are linked to one another exclusively via single bonds and for which, on account of this single bonding, the hydrocarbons are much less reactive than the corresponding olefins. In contrast to the olefins, therefore, alkanes are seldom utilized as starting material for chemical reactions, instead serving mostly as fuels or propellants. The $C_4$ alkanes include n-butane and isobutane. The butanes are present in the majority of industrially available $C_4$ cuts and their behaviour in the oligomerization is inert.

The preparation of $C_8$ olefin and of $C_{12}$ olefin from the butenes present in $C_4$ cuts is economically attractive and is therefore operated on the industrial scale. The $C_8$ olefins obtained can in fact be converted by hydroformylation with carbon monoxide and hydrogen into $C_9$ aldehydes, which are processed further by subsequent hydrogenation to give $C_9$ alcohols. The $C_9$ alcohols in turn constitute a prized starting material for the production of plasticizers for PVC. In a similar way, the $C_{12}$ olefins formed in the oligomerization of three butenes are processed further by hydroformylation and hydrogenation to give $C_{13}$ alcohols. The $C_{13}$ alcohols are a precursor in the production of detergents. Since the demand for olefins having more than twelve carbon atoms is much less than that for olefins of eight or twelve carbon atoms, the present oligomerization of $C_4$ olefins is operated in such a way as to form, substantially, $C_8$ olefins and $C_{12}$ olefins.

One process for the oligomerization of $C_4$ olefins that is practised industrially is that known as the OCTOL process. A comprehensive description of this process is found in the non-patent literature, including for example:

B. Scholz: The HÜLS OCTOL Process: Heterogeneously catalyzed dimerization of n-butenes and other olefins. DGMK meeting at Karlsruhe, published in Erdöl, Erdgas, Kohle, April 1989, pages 21 and 22.

R. H. Friedlander, D. J. Ward, F. Obenaus, F. Nierlich, J. Neumeister: Make plasticizer olefins via n-butene dimerization. Hydrocarbon Processing, February 1986, pages 31 to 33.

F. Nierlich: Oligomerize for better gasoline. Hydrocarbon Processing, February 1992, pages 45 to 46.

Within the patent literature, for example, DE102008007081A1 describes an oligomerization based on the OCTOL process. EP1029839A1 describes a method for fractionating the $C_8$ olefins formed in the OCTOL process.

The OCTOL process is generally carried out as a multistage process by means of a reactor cascade comprising serially connected reaction zones or reactors in a number which corresponds to the number of stages. Between each of the individual reaction zones there is a distillation column provided, which separates the oligomers formed previously from the oligomerizate from the unreacted butenes and removes them. The unreacted butenes are partly returned to the preceding oligomerization, while the other part is supplied to the subsequent oligomerization. The OCTOL process therefore encompasses a multiply traversed step sequence composed of the following four individual steps:

a) providing of a butene-containing hydrocarbon mixture;
b) oligomerizing;
c) removing of the unreacted butenes from the oligomerizate;
d) recycling of part of the unreacted butenes to the preceding oligomerization, and of the other part to the subsequent oligomerization.

As a result of the recycling of the unreacted butenes, there is always an oversupply of butenes in the initial stages, and accordingly in the individual oligomerization stages there is never complete conversion into $C_8$, $C_{12}$ and $C_{12+}$ olefins. Only the entire OCTOL process, which depending on economic efficiency is carried out in two to six stages, is able overall to result in near-complete conversion of the butenes employed.

A further multi-stage process for the oligomerization of $C_4$ olefins is known from WO99/25668 or from DE10015002A1. Here, the olefin streams provided are diluted with recycled butanes, in order to simplify the removal of heat from the exothermic reaction via the reactor effluent.

Depending on the way in which the individual n-butene molecules join together in the course of the oligomerization, an oligomerizate is obtained with a different degree of branching. The degree of branching is described by the Iso index, which states the average number of methyl groups per $C_8$ molecule in the isomer mixture. For dibutene, the Iso index is defined as follows:

Iso index=(weight fraction of methylheptenes+
2*weight fraction of dimethylhexenes)/100

Accordingly, n-octenes with 0, methylheptenes with 1 and dimethylhexenes with 2 contribute to the Iso index of a product mixture comprising $C_8$ olefins. The lower the Iso index, the less branched the construction of the molecules within the mixture.

For the properties of the plasticizer, though, a critical part is played by the degree of branching of the olefinic starting mixture which is used for the preparation of the plasticizer alcohol: the higher the linearity of the $C_8$ olefin mixture, the better the properties of the $C_9$ plasticizer alcohol prepared from it. In the case of the preparation of dibutene as a starting product for plasticizer alcohols, therefore, the aim is to run the oligomerization so as to obtain a $C_8$ product mixture with as small as possible an Iso index.

Accordingly, for example, in EP1029839A1, the fractionation of the oligomerizates is set up so that the $C_8$ product mixture removed has as low an Iso index as possible.

In WO99/25668A1, however, a low Iso index is achieved by returning the unreacted butene and butane removed from the oligomerizate to the oligomerization in quantities such that the maximum amount of oligomers in the converted reaction mixture does not exceed 25 wt % at any point in the reactor cascade.

Both processes used a "raffinate II" with a high 1-butene fraction as starting mixture for the oligomerization. "Raffinate II" is commonly understood to refer to a butane/butene mixture which is obtained from "C4 cuts" which come from steamcrackers and from which butadiene and isobutene have already been removed. Typical raffinate II, accordingly, contains around 30 wt % of 1-butene.

It can be shown that a high fraction of 1-butene in the hydrocarbon mixture provided is beneficial to the linearity of the oligomerizate. It is therefore no surprise that, starting from the raffinate II raw material, WO99/25668A1 prepares $C_8$ product mixtures with an Iso index of less than 1.

In his above-cited essay "Oligomerize for better gasoline", Nierlich as well emphasizes how raffinate II is a more suitable starting material for oligomerization than raffinate III. "Raffinate III" is obtained by removing 1-butene from raffinate II, and so its 1-butene content is much lower than that of raffinate II.

Nierlich considers FCC-$C_4$ to be suitable for preparing dibutene only after prior hydroisomerization:
F. Nierlich: Integrated tert. butyl Alcohol/Di-n-butenes Production from FCC C4's. Erdöl, Erdgas, Kohle. Vol. 103 (1987), pages 486 to 489.

On account of the increasing scarcity of raw materials that has now occurred, however, the petrochemical product raffinate II is no longer universally available in large quantities and on favourable terms. Thus alternative raw material sources yield $C_4$ olefin mixtures which in some cases now contain almost no 1-butene, but instead predominantly 2-butene.

It was an object of the invention, therefore, to specify a process for oligomerizing butenes that allows the preparation of $C_8$ olefins, having a low Iso index favourable for plasticizer production, even when the substrate $C_4$ stream contains only very small amounts of the linearity-promoting 1-butene. Furthermore, the desired process is to have a high selectivity in the direction of the $C_8$ olefins, in order to dimerize as much as possible of the butenes employed; the reactions forming $C_{12}$ and $C_{12+}$ oligomers are to be minimized as far as possible.

It has now been found that the stated objective can be achieved with an oligomerization process of the generic type specified at the outset if, in the step sequence carried out for the first time, the conversion of butenes, assessed over the first reaction zone, is limited to a first limit value of between 5 and 40 wt %.

Thus it has surprisingly been shown that limiting the conversion in the first stage leads to $C_8$ product mixtures having an Iso index of less than 1.2 even when, in the step sequence carried out for the first time, the concentration of 1-butene in the hydrocarbon mixture provided, based on the concentration of linear butenes, is less than or equal to the equilibrium concentration of 1-butene, resulting from the reaction temperature of the step sequence carried out for the first time, within the fraction of the linear butenes present in the hydrocarbon mixture provided for the first time.

The reason why this finding is surprising is that there had been no prior reports of any butene oligomerization process which, even with such low concentrations of 1-butene in the oligomerization feed, still led to a $C_8$ product mixture having a passable Iso index. Thus the only oligomerization processes vaunted hitherto in the state of the art had been processes which were geared to a high conversion and for that reason aimed at extremely high reaction temperatures. Since only $C_4$ streams with a high 1-butene content were used in the past, it was possible nevertheless to obtain $C_8$ oligomer mixtures with low levels of branching.

The conversion in the first stage, assessed directly over the first reaction zone, is limited preferably to 10 to 38 wt % and very preferably to a first limit value of between 10 and 36 wt %.

By conversion is meant the percentage mass fraction of the butenes that is converted to butene oligomers within the assessment boundary under consideration.

The invention accordingly provides a process for preparing $C_8$ olefins and $C_{12}$ olefins by oligomerization of butenes, which comprises the following step sequence:
 a) providing of a hydrocarbon mixture comprising at least one 2-butene and also at least one further linear butene other than this 2-butene;
 b) oligomerizing of a part of the butenes present in the hydrocarbon mixture, to give $C_8$ olefins and to give $C_{12}$ olefins and optionally to give $C_{12+}$ olefins, by contacting of the hydrocarbon mixture with an oligomerization catalyst arranged in a reaction zone, at a reaction temperature prevailing in the reaction zone, to give an oligomerizate comprising the prepared oligomers and the unreacted butenes;
 c) removing of the unreacted butenes from the oligomerizate;
 d) optionally, recycling of a part of the removed unreacted butenes to the preceding oligomerization;
 the step sequence being carried out at least once with inclusion of the "recycling" step,
 where the process is carried out with the provisos
 that in the step sequence carried out for the first time, the concentration of 1-butene in the provided hydrocarbon mixture, based on the concentration of linear butenes, is less than or equal to the equilibrium concentration of 1-butene, resulting from the reaction temperature of the step sequence carried out for the first time, within the fraction of the linear butenes present in the hydrocarbon mixture provided for the first time,
 that the $C_8$ olefins prepared are obtained as a $C_8$ product mixture whose Iso index is less than 1.2,
 and this objective is achieved
 in that in the step sequence carried out for the first time, the conversion of butenes, assessed directly over the first reaction zone, is limited to a first limit value of between 5 and 40 wt %, this value lying preferably between 10 and 38 wt % and very preferably between 10 and 36 wt %.

The limitation on the conversion in the individual stages is accomplished in accordance with the invention by a strict limitation on the reaction temperature within the individual stages and/or by a strict circulation regime. Low reaction temperatures and a high recycle fraction effectively limit the conversion of butenes as assessed directly at the reaction zone.

Achieving a sufficiently high butene conversion across the process overall in spite of the severe limitation on conversion in the first step necessitates an appropriately high number of reaction stages or step sequences. The number of stages, though, cannot be infinite, since that would significantly increase the capital costs and operating costs of the oligomerization plant and so would render the overall process uneconomic.

In some investment situations, therefore, it may be economically efficient to operate a two-stage process in which the "providing, oligomerizing, removing and recycling" step sequence is carried out at least twice one after another, and in the second step sequence carried out, the conversion of butenes assessed directly on the second reaction zone is limited to a second limit value of between 5 and 50 wt %, this value lying preferably between 10 and 40 wt %.

Where higher overall conversions are required, the process can be performed in three stages, so that the "providing, oligomerizing, removing and recycling" step sequence is carried out three times one after another, and in the third step sequence carried out, the conversion of butenes assessed directly at the third reaction zone is limited to a third limit value of between 5 and 65 wt %, this value lying preferably between 20 and 60 wt %.

Even more efficient utilization of feedstock is achieved in the case of a four-stage oligomerization, in which the "providing, oligomerizing, removing and recycling" step sequence is carried out four times one after another, and in the fourth step sequence carried out, the conversion of butenes assessed directly at the fourth reaction zone is limited to a fourth limit value of between 5 and 80 wt %, this value lying preferably between 20 and 70 wt %.

A five-stage oligomerization, in which the "providing, oligomerizing, removing and recycling" step sequence is carried out five times one after another, will be situated—given the present costs of raw materials and investment costs—at the limits of economic rationality, with the consequence that presently a four-stage process regime will tend to be preferred. Since in the future, however, a five-stage oligomerization may also well be economical, it may be noted that in the fifth step sequence carried out, the conversion of butenes assessed directly at the fifth reaction zone should be limited to a fifth limit value of between 5 and 95 wt %, with the fifth limit value lying preferably between 20 and 80 wt %.

Depending on the number of reaction stages selected, the overall conversion of butenes achieved after all of the step sequences have been carried out is between 5 and 100 wt %. The number of stages is selected more particularly so as to achieve an overall conversion of between 20 and 100 wt % and very preferably between 30 and 95 wt %.

As already mentioned, the conversion can be limited effectively by a lowering of the reaction temperature in the respective oligomerization. A low reaction temperature in the sense of the invention is located between 40° C. and 140° C. With preference, however, the reaction temperature in the individual oligomerizations is limited to values of between 45° C. and 120° C. and very preferably between 50° C. and 100° C.

The temperature limitation is accomplished preferably by cooling of the reaction zone by means of an external cooling medium, which is not itself present in the oligomerization. The heat of reaction is transmitted to the cooling medium via the boundary of the reaction zone (in general, the reactor walls). Water is a preferred cooling medium. Alternatively an organic heat-transfer oil can be used, such as Marlotherm® from Sasol Germany GmbH, for example.

The process is preferably conducted such that in terms of the $C_8$ olefins prepared, a selectivity is achieved of more than 80, more particularly more than 82 and very preferably more than 84 wt %. This means that more than the stated weight fractions of the oligomers prepared are $C_8$ olefins. The reaction in the direction of the $C_{12}$ and $C_{12+}$ olefins is therefore minimized, ultimately also as a result of the low temperatures.

In the same way as the butenes used are present as different structural isomers, $C_8$ olefins as well are formed with different structural isomers. The $C_8$ olefins prepared, accordingly, are generally n-octenes, methylheptenes and dimethylhexenes. In order to obtain an Iso index that is favourable for plasticizer production, the $C_8$ olefins prepared ought to have the following composition, adding up to 100 wt %:

n-octenes: 10 to 25 wt %, preferably 12 to 20 wt % and more preferably 14 to 20 wt %;
methylheptenes: 50 to 80 wt %, preferably 55 to 75 wt % and more preferably 60 to 70 wt %;
dimethylhexenes: 10 to 30 wt %, preferably 10 to 25 wt % and more preferably 10 to 20 wt %.

With a composition of this kind, a $C_8$ product mixture is then obtained whose Iso index is below 1.1 and very preferably below 1.05.

As already mentioned, a feature of the process of the invention is that it allows the processing of $C_4$ streams with a very low 1-butene content into a highly linear $C_8$ product mixture. Particularly noteworthy is the fact that the 1-butene content relative to the 2-butenes content may be situated below the thermodynamic equilibrium of the linear butenes, as determined in accordance with the conditions within the first step sequence.

Accordingly, $C_4$ feedstock mixtures with an extremely low 1-butene fraction can be utilized. The invention in fact permits the use of $C_4$ feedstock mixtures which are virtually free of 1-butene. This makes the oligomerization process of the invention better adapted to present raw material situations than is the conventional OCTOL process.

Preferably, therefore, the hydrocarbon mixture provided for the first time is a reactant mixture having the following composition, which adds up to 100 wt %:

1-butene: less than 10 wt %, preferably less than 5 wt % and more preferably less than 2 wt %
2-butenes: 20 to 90 wt %
isobutene: less than 5 wt %, preferably less than 1 wt %
n-butane: less than 80 wt %
isobutane: less than 80 wt %
others: less than 5 wt %, preferably less than 2 wt %

A reactant mixture of this kind might be, for example, a raffinate III or a non-upgraded $C_4$ stream from a fluid-catalytic cracker.

Since the oligomerization process of the invention is intended for large-scale industrial use, it is suitable without restriction for continuous operation. It is preferably carried out, accordingly, in a plant within which exactly one reaction zone is assigned to each step sequence carried out. A reactor cascade represents one such plant. The reaction zone may be formed by one or more reactors, connected in parallel or serially. For the definition of a step sequence in the sense of the present invention it is not the number of reactors which is critical, but rather the number of combinations of oligomerization and subsequent removal.

It is self-evident that in each traversed step sequence apart from the last step sequence, the non-recycled part of the removed unreacted butenes is provided as a hydrocarbon mixture for the subsequent step sequence.

The non-recycled part of the removed unreacted butenes of the last step sequence is, accordingly, not subjected to a further oligomerization, but is instead productively utilized in other ways. Appropriate here are the following utilization possibilities:
 a) total hydrogenation to give a butane mixture;
 b) oxidative or non-oxidative dehydrogenation to butadiene;
 c) hydroformylation to pentanals;
 d) oxidation in particular to maleic anhydride;
 e) metathesis;
 f) hydration to butanols;
 g) alkylation;
 h) isomerization;
 i) addition reaction of alcohols to ethers;
 j) carbonylation;
 k) cracking in a steamcracker or in a fluid-catalytic cracker to give hydrocarbons having less than four carbon atoms;
 l) combustion to give thermal energy.

In accordance with the invention, unreacted butenes are removed from the oligomerizate downstream of each oligomerization step, leaving the oligomers behind. The removal is by distillation in a conventional way. It removes the unreacted butenes from the oligomerizate at the top, leaving the longer-chain oligomers in the liquid phase. The removal by distillation is comparatively simple to bring about, since there is a fairly large difference in boiling point between the unreacted $C_4$ olefins and the $C_8$, $C_{12}$ and $C_{12+}$ oligomers.

The oligomers obtained in the individual step sequences are combined and subsequently separated, in a further distillation, into the desired $C_8$ product mixture, into a $C_{12}$ product mixture and into a $C_{12+}$ product mixture. The combining of the individual product mixtures may in this case preferably also take place in the column downstream of the last oligomerization.

Further aspects of the present invention will become apparent from the description that now follows of a number of embodiments. For this purpose, the following figures offer the following schematic representations.

Figure 1:
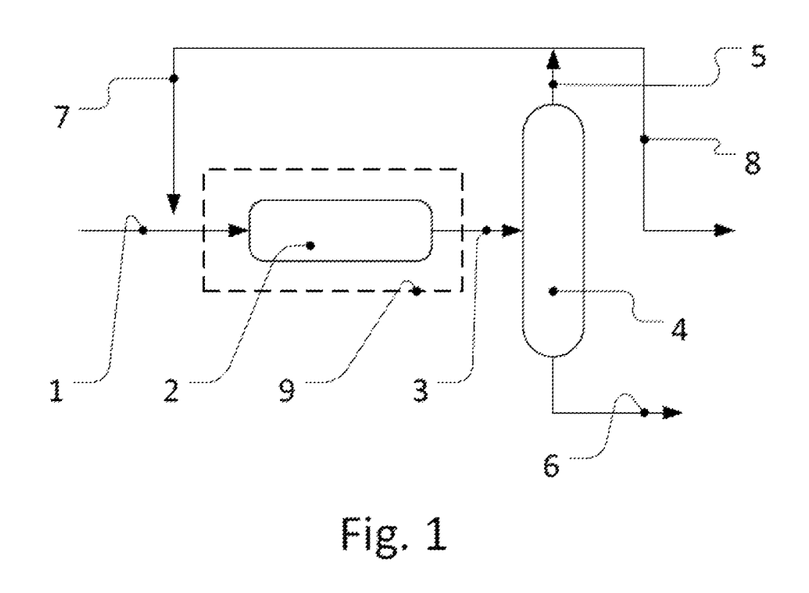
FIG. 1: one-stage process.

FIG. 1 shows a simplified flow diagram of an oligomerization process of the invention. Starting material is a reactant mixture 1, which comes, for example, from a fluid-catalytic petroleum cracker, may have been subjected to preliminary purification, and is provided as a continuous stream of material. The reactant mixture 1 comprises a mixture of hydrocarbons having four carbon atoms, including the $C_4$ olefins, 1-butene, cis-2-butene, trans-2-butene and isobutene, and also the $C_4$ alkanes n-butane and isobutane. No attention is paid here to other organic or inorganic constituents which typically occur within $C_4$ cuts. The particular nature of the reactant mixture 1 provided is that its 1-butene content is unusually low. The composition of reactant mixture 1 is as follows:
 1-butene: less than 5 wt %
 2-butenes: 20 to 90 wt %
 isobutene: less than 1 wt %
 n-butane: less than 80 wt %
 isobutane: less than 80 wt %
 others: less than 2 wt %

Reactant mixture 1 is passed into a reaction zone 2. At the reaction temperature prevailing there, it comes into contact with an oligomerization catalyst arranged in the reaction zone 2, and so some of the butenes present in the reactant mixture 1 react with one another to give oligomers, and are taken off from the reaction zone 2 in an oligomerizate 3. The oligomerizate is a mixture of the oligomers formed, of the unreacted butenes, and of those constituents of the reactant mixture that behave inertly in the reaction, such as the butanes.

The oligomers include $C_8$ olefins such as n-octenes, methylheptenes and dimethylhexenes which are formed by the oligomerization of two $C_4$ olefins. Where three butenes or one butene and one previously formed octene oligomerize with one another, the products are $C_{12}$ olefins (dodecenes). Four butenes oligomerizing with one another, or two butenes and one previously formed octene, or two previously formed octenes or one butene and one previously formed dodecene, lead to $C_{16}$ olefins.

The oligomerization carried out in reaction zone 2 forms predominantly $C_8$ olefins; $C_{12}$ olefins are the greatest by-product. The olefins with more than twelve carbon atoms are formed only in comparatively small fractions and are referred to collectively as $C_{12+}$ olefins.

The composition of the oligomerizate, adding up to 100 wt %, is typically as follows:
 butanes less than 80 wt %
 1-butene 1 to 5 wt %
 2-butenes 10 to 80 wt %
 n-octenes 1 to 10 wt %
 methylheptenes 5 to 40 wt %
 dimethylhexenes 1 to 15 wt %
 $C_{12}$ olefins 1 to 10 Wt %
 $C_{12+}$ olefins 0.1 to 2 wt %

The oligomerization catalyst, which is not shown in the figures, is a heterogeneous, nickel-containing catalyst. Employed with preference is a supported catalyst comprising a support material such as silicon dioxide or aluminium oxide or mixtures thereof, or aluminosilicates or zeolites, for example. The supports may comprise sulphur in the form of sulphate, sulphide or other types of compound. Suitable oligomerization catalysts are known in the technical literature and are described for example in DE 4339713 A1 or in WO 2001/37989 A2 or in WO 2011/000697 A1.

For the preparation of the supported nickel catalysts used there are a variety of ways. For example, such catalysts may be prepared by joint precipitation of nickel compounds and support material (i.e. aluminium compounds and/or silicon compounds), filtration and subsequent heat treatment. Another option is to apply nickel compounds to a suitable support material, by impregnation or sprayed application, for example, with subsequent calcining. To prepare the catalysts by the impregnating method, nickel compounds such as nickel nitrate, nickel chloride or amine complexes, for example, may be used. Support materials used are preferably commercially available catalyst supports such as, for example, amorphous mixed silicon aluminium oxides carrying the designation "Grace DAVICAT", available from Grace, or zeolites (e.g. MCM41) from Mobil Oil.

Especially preferred is the use of titanium free supports and supported catalysts, consisting substantially of nickel oxide, aluminium oxide and silicon oxide. These catalysts contain preferably 5 to 50 mass % nickel, more particularly 10 to 30 mass % nickel. The aluminium contents are in the range from 5 to 30 mass %, more particularly in the range from 7 to 20 mass %. The fractions of silicon are in the range from 10 to 40 mass %, with the range from 20 to 30 mass % being particularly preferred. The stated mass fractions are based on the total metal content. As further components, these catalysts may contain 0.1 to 2 mass % of alkali metal oxide, alkaline earth metal oxide, lanthanum oxide or oxides of the rare earths, and optionally shaping auxiliaries.

In macroscopic terms, the nickel catalyst used in accordance with the invention is employed in a form in which it presents a low resistance to flow. The oligomerization catalyst is preferably in the form of shaped bodies such as granules, pellets, tablets, cylinders, beads, strand extrudates or rings.

In terms of apparatus, the reaction zone 2 is implemented preferably as a shell-and-tube reactor or as a serial or parallel connection of a plurality of reactors. Even when the oligomerization is carried out in a plurality of serially connected reactors, the oligomerization step here is a single step, since in the terminology of the present invention, an oligomerization step always concludes with a removal step. More later on this in reference to FIG. 2.

The shell-and-tube reactor preferably employed comprises a multiplicity of flow-traversed tubes with a catalyst filling. The reactant mixture 1 flows in at the start of the tubes, optionally in a mixture with recycle stream 7; at the end of the tubes, the oligomerizate 3 is taken off. The heat of reaction that forms in the course of the exothermic oligomerization reaction is taken off preferably not via the outflowing oligomerizate 3, but instead via an external cooling medium (not shown). The cooling medium flows through a jacket surrounding the tube bundle, allowing heat exchange without exchange of matter to take place between the reaction mixture and the cooling medium. The cooling medium does not participate in the reaction; accordingly, the shell-and-tube reactor also fulfils the function of a heat exchanger. At its most simple, the cooling medium is suitably water or an organic heat-transfer fluid such as Marlotherm® from Sasol Germany GmbH, for example.

Setting the reaction temperature within the oligomerization by means of the cooling medium is of particular interest since in accordance with the invention, the limitation of the reaction temperature represents an important measure for limiting the conversion. Very preferably, therefore, the reaction temperature is to be limited to a comparatively low figure of between 50 and 100° C., this being made possible by the use of the external cooling medium.

The pressure within the reaction zone is selected such that the $C_4$ hydrocarbons present are in liquid phase. The pressure is set accordingly to between 0.1 to 70 MPa, preferably from 0.1 to 10 and very preferably from 0.5 to 4 MPa.

The specific catalyst space velocity (WHSV) is between 0.1 and 5 $min^{-1}$, preferably 0.2 and 3 $min^{-1}$.

The oligomerizate 3 taken off from the reaction zone 2 is then introduced into a separating device in the form of a distillation column 4, in which it is separated conventionally by distillation into a top stream 5, containing the inert butanes and the butenes not reacted in the oligomerization, and into a liquid phase stream 6, containing the oligomers prepared. The distillation takes place preferably under a pressure of 0.1 to 1 MPa, preferably under 0.2 to 0.5 MPa. Because of the considerable difference in the molecular weight and the resultant distinct difference in the boiling points between the $C_4$ hydrocarbons taken off at the top and the oligomers with eight or more hydrocarbons in the liquid phase, separation within the distillation column 4 is achieved with comparatively little technical complexity, and so more detailed comments are unnecessary. Further information on the design of the distillative purification of oligomerizates is found in EP1029839A1.

The top stream 5 containing the unreacted butenes is divided into a recycle stream 7 and a transfer stream 8. The recycle stream 7 is mixed with the reactant stream 1 originally provided, and supplied again to the oligomerization 2. The transfer stream 8 is passed on for further production utilization of the butenes and butanes it contains (not shown). The proportion of the top product recycled, in other words the division ratio of the streams 7 to 5 and 8 to 5, is a further parameter, alongside the reaction temperature, for limiting the conversion within the reaction zone 2. In accordance with the invention, indeed, the conversion within the reaction zone 2 is limited to a first limit value of between 5 and 40 wt %. The stated conversion is assessed immediately at the reaction zone 2, in order words within the assessment boundary 9 drawn with dashed lines. What is meant is therefore the conversion "per pass" based on the reactor feed, which is composed additively of the fresh feed 1 and the (optional) recycle stream 7.

The conversion within the assessment boundary 9 is limited on the one hand by the restriction on the reaction temperature through appropriate cooling of the reaction zone 2 via the cooling medium, and also via the size of the recycle stream 7.

In the liquid phase of the distillation column 4, the liquid phase stream 6 is taken off, containing the oligomers prepared. These oligomers will also be separated in accordance with their molecular weight (not shown in FIG. 1).

The oligomerization process represented in FIG. 1 constitutes the simplest embodiment of the invention, in which the step sequence of providing, oligomerizing, removing and optionally recycling is run through only a single time. On account of the inventive limitation on the conversion within the assessment boundary 9, drawn in with dashed lines, to not more than 40%, it is possible, without recycle stream 7, to achieve only an overall conversion of 40% assessed over the entire process. In order to increase the overall conversion, the stated step sequence is performed preferably with recycle stream 7 and/or a number of times after one another, for example twice as shown in FIG. 2.

Figure 2:
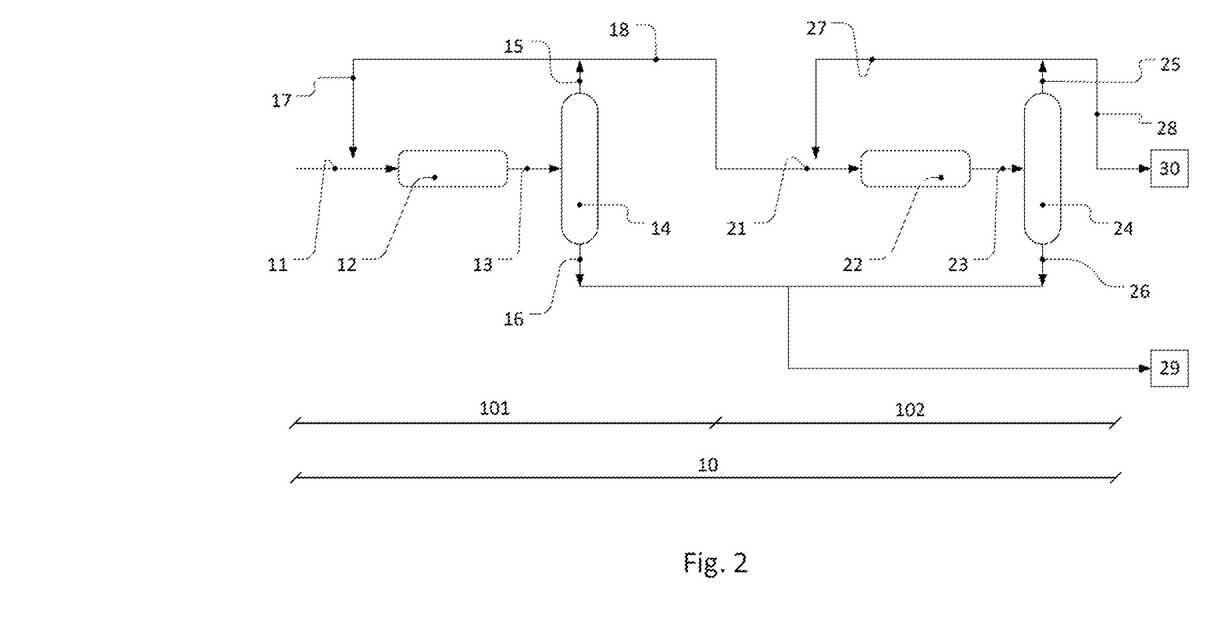
FIG. 2: two-stage process.

In the two-stage process of FIG. 2, the step sequence represented in FIG. 1 is run through twice one after another, and so the overall process 10 is subdivided into a first step sequence 101 and a second step sequence 102. Since the overall process 10 is operated continuously, the apparatus required in each step sequence is present twice, accordingly, and is connected serially. This is referred to as a reactor cascade.

Within the step sequence 101 run through for the first time, a $C_4$ hydrocarbon mixture is provided for the first time as reactant mixture 11, and is then oligomerized in a first reaction zone 12, and the first oligomerizate 13 obtained is separated in a first distillation column 14 into a first top stream 15 and a first liquid phase stream 16. One part of the first top stream 15 is returned to the preceding oligomerization 12, for conversion of butenes not reacted there so far, while the other part is transferred as a first transfer stream 18 into the second step sequence 102. In this second sequence it serves as provided hydrocarbon mixture 21 for the second stage of the oligomerization, which takes place in a second reaction zone 22. The second oligomerizate 23 obtained therein is again separated, in a second distillation column 24, into a second top stream 25 and a second liquid phase stream 26. The top stream 25 of the second distillation column 24 is divided into a second recycle stream 27 and a second transfer stream 28.

The liquid phase stream 26 of the second distillation column 24 is combined with the first liquid phase stream 16, and supplied for joint fractionation 29 of the oligomers present therein. Possible embodiments of the fractionation 29 are elucidated with reference to FIGS. 3 and 4.

The part of the removed unreacted butenes not recycled to the second and hence last step sequence 102 is not oligomerized any more, and is passed on with the second transfer stream 28 for productive utilization 30. Utilization 30 consists at its most simple of the combustion of the non-recycled top product of the last column 24. If a fluid-catalytic cracker or steamcracker is available in the plant vicinity, it is appropriate to pass stream 28 back into the cracker and to separate it there into hydrocarbons having less than four carbon atoms. Where no such cracker is available, the butenes present in the non-recycled second transfer stream 28 may be subjected to total hydrogenation, with the consequence that a butane mixture is obtained in the utilization 30, and is suitable as propellant gas or fuel gas for private use. There are also other utilization possibilities for the unreacted butenes per se, their profitability being dependent on the selling situation and on the composition of the stream of material 28 leaving the oligomerization.

Figure 3:
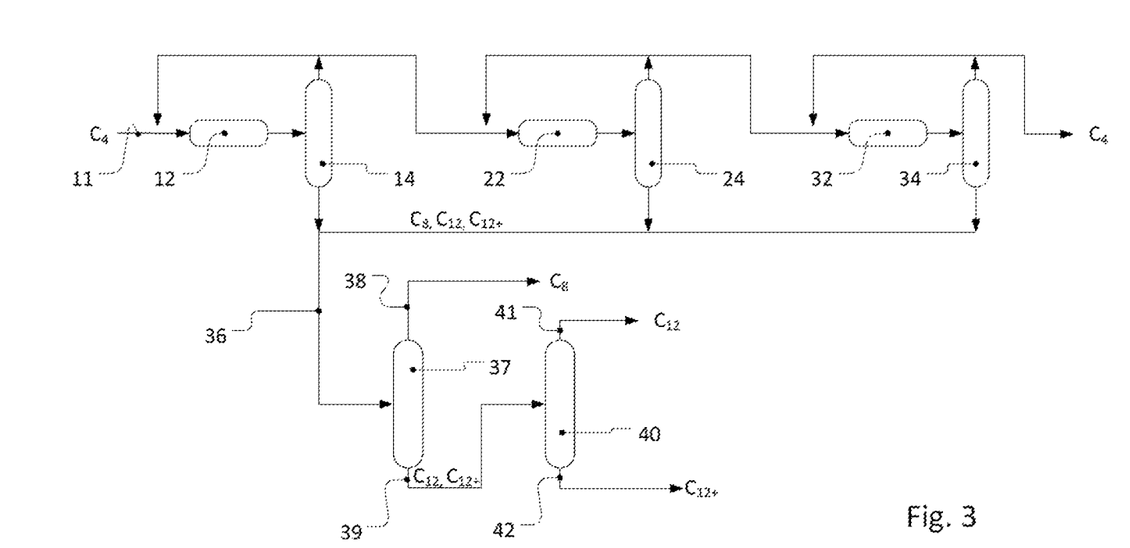
FIG. 3: three-stage process.

FIG. 3 shows a further embodiment of the invention, in which the $C_4$ hydrocarbon mixture 11 provided the first time is oligomerized by triple runthrough of the step sequence in a total of three reaction zones 12, 22, 32. Each reaction zone 12, 22, 32 is assigned its own distillation column 14, 24, 34, in which the oligomers prepared in each preceding oligomerization run are removed. For this purpose, the liquid phase streams of the distillation columns 14, 24, 34 are combined and supplied to a joint fractionation.

For the fractionation of the oligomers prepared, the combined liquid phase streams 36 are first of all passed into a $C_8$ column 37. In this column, the actual target product of the process, a $C_8$ product mixture, is removed at the top by distillation. The $C_8$ product mixture consists almost exclusively of $C_8$ olefins, with the following composition, which adds up to 100 wt %:
  n-octenes: 10 to 25 wt %
  methylheptenes: 50 to 80 wt %
  dimethylhexenes: 10 to 30 wt %.

The Iso index of the $C_8$ product mixture 38 obtained therein is less than 1.1.

About 80% of all the butene oligomers formed are dibutenes and are within the $C_8$ product mixture, making the selectivity of the process very high in terms of the desired target product ($C_8$ olefins).

The liquid phase product 39 of the $C_8$ column 37, containing the oligomers prepared and having twelve and more than twelve carbon atoms, is supplied to a $C_{12}$ column 40, where it is separated into a $C_{12}$ product mixture 41, which is taken off at the top, and into a $C_{12+}$ product mixture 42 in the liquid phase of the $C_{12}$ column 40.

About 7% to 17% of the oligomers formed are the $C_{12}$ olefins present in the $C_{12}$ product mixture 41. The $C_{12}$ product mixture, which is still formed to a significant extent, can be used for the production of detergent alcohols.

The olefins having more than twelve carbon atoms which are present in the $C_{12+}$ product mixture can be hydrogenated and admixed to light heating oil or to diesel fuel.

Figure 4:
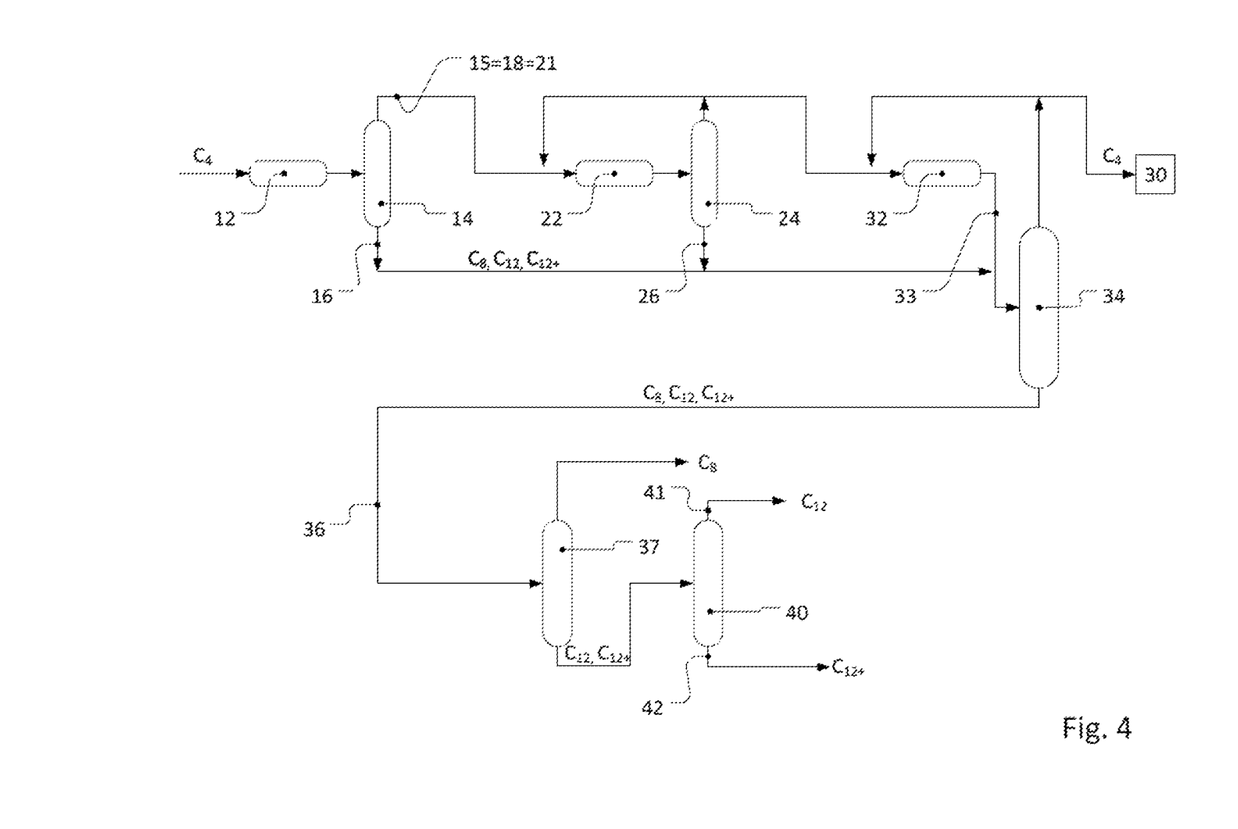
FIG. 4: three-stage process with product combination before the last separating column.

FIG. 4 shows another inventive variant of a three-stage process. In the case of the embodiment shown in FIG. 4, the optional step of "recycling" is omitted within the step sequence carried out the first time. Accordingly, the entire top stream 15 of the first distillation column 14 is transferred as a first transfer stream 18 into the second step sequence, to provide the hydrocarbon mixture 21 needed for the second stage.

Within the context of the invention, it will also be possible to omit the recycling in a stage other than the first stage, or it is possible even to carry out a number of step sequences without the "recycling step". In at least one step sequence, however, recycling should be provided. In the case of a one-stage process, the recycling is carried out in the first and only step sequence, as a logical necessity.

Relative to the embodiment of a three-stage process shown in FIG. 3, the fractionation of the oligomers prepared is performed differently in this case: accordingly, the liquid phase streams 16 and 26 of the first and second distillation columns 14, 24 are combined with the oligomerizate 33 of the third stage and then supplied to the third distillation column 34. The third distillation column 34, accordingly, is given a greater size than in the embodiment shown in FIG. 3. The liquid phase stream 36 of the third distillation column 34 then corresponds to the combined liquid phase streams 36 of the embodiment shown in FIG. 3. The fractionation of the oligomers from the combined liquid phase streams 36 corresponds to the embodiment shown in FIG. 3.

EXAMPLE 1 (NOT INVENTIVE)

The non-inventive example 1 was conducted in accordance with WO 99/25668 A1 in a largely adiabatically operated tube reactor with the following dimensions: length 2.0 m, internal diameter 32.8 mm. The reaction was carried out under an absolute pressure of 3 MPa in the liquid phase.

The feedstock used was a hydrocarbon mixture containing the following components, adding up to 100 wt %:
  1-butene 25%
  2-butene 51%
  isobutene less than 1%
  isobutane less than 2%
  n-butane more than 21%

Contrary to the teaching of the present invention, the mixture therefore contained an amount of 1-butene which is above the concentration of 1-butene that comes about in the thermodynamic equilibrium of the n-butenes at reaction temperature (in this case, reactor entry temperature 60° C.). At a temperature of 60° C., this value is about 4.1% in the overall mixture, or 5.4% within the n-butene fraction.

A part of the stream of the unreacted butenes was returned to the reactor (recycle); the recycled quantities were selected, in accordance with the teaching of WO 99/25668 A1, such that the oligomer concentration does not exceed 25% at any point in the reactor and does not fall below 10% in the reactor effluent. The individual concentrations of the oligomers can be found in Table 1.

The catalyst used was a material prepared in accordance with Example 1 of WO 2011/00697 A1 and aftertreated in accordance with Example 4 of the same publication.

The product stream was analysed for its composition by means of gas chromatography (GC). To identify the octene skeleton isomers, a hydrogenating GC analysis method was used, in which the oligomeric olefins are first hydrogenated to alkanes. The resultant alkanes are then separated chromatographically and detected. It is possible to differentiate between three relevant $C_8$ isomers: n-octane (formed from n-octenes), methylheptane (formed from methylheptenes) and dimethylhexane (formed from dimethylhexenes). The composition of the hydrogenated $C_8$ mixture is compiled in Table 1.

EXAMPLES 2 TO 5 (NOT INVENTIVE)

The examples were carried out in accordance with WO 99/25668 A1 in a largely adiabatically operated tube reactor with the following dimensions: length 2.0 m, internal diameter 32.8 mm. The reaction was carried out under an absolute pressure of 3 MPa in the liquid phase. Feedstocks used were two hydrocarbon mixtures with different 1-butene/2-butene ratios but with a constant total amount of n-butenes. The concentrations of the n-butenes are given in Table 1. In addition, the mixtures contained the following components, which add up to 100 wt %:
  isobutane less than 2%
  n-Butane more than 21%
  Isobutene less than 1%

An of the mixtures therefore contained 1-butene amounts below the 1-butene concentration which comes about in the thermodynamic equilibrium of the n-butenes at the reaction temperature, which is set here at 60° C. and measured at the reactor entry.

A part of the stream of the unreacted butenes was returned to the reactor (recycle), as described in Example 1.

The catalyst used was the same material as in Example 1.

TABLE 1

Analysis of Examples 1 to 5

| Example No. | 1 | 2 | 3 | 4 | 5 |
|---|---|---|---|---|---|
| Fresh feed [g/h] | 850 | 850 | 850 | 850 | 850 |
| 1-Butene concentration in fresh feed [wt %] | 25.0 | 0.5 | 0.5 | 4.0 | 4.0 |
| 2-Butene concentration in fresh feed [wt %] | 51.0 | 75.5 | 75.5 | 72.0 | 72.0 |
| Recycle amount [g/h] | 1500 | 4200 | 1500 | 4200 | 1500 |
| Entry temperature [° C.] | 60.0 | 60.0 | 60.0 | 60.0 | 60.0 |
| Exit temperature [° C.] | 120.4 | 96.3 | 119.3 | 96.6 | 119.0 |
| Per pass conversion [wt %] | 50.7 | 22.8 | 45.9 | 23.4 | 46.4 |
| Concentration of oligomers in reactor effluent [wt %] | 23.7 | 10.3 | 22.9 | 10.4 | 23.0 |
| Total conversion [%] | 86.5 | 80.3 | 83.3 | 81.1 | 83.7 |
| $C_8$ selectivity [%] | 80.6 | 86.9 | 81.9 | 86.7 | 81.7 |
| Mass fractions in hydrogenated $C_8$ mixture [wt %] | | | | | |
| n-Octane | 17.2 | 11.7 | 12.6 | 12.2 | 13.1 |
| Methylheptane | 62.8 | 68.0 | 61.6 | 68.0 | 62.4 |
| Dimethylhexane | 18.9 | 19.2 | 24.7 | 18.8 | 23.4 |
| Iso index | 1.017 | 1.075 | 1.123 | 1.067 | 1.105 |

EXAMPLES 6 TO 12 (INVENTIVE)

Examples 6 to 12 were carried out in a three-stage reactor cascade of largely isothermally operated tube reactors with the following dimensions: length 2.0 m, internal diameter 32.8 mm. The oligomerization was carried out in each case under an absolute pressure of 3 MPa in the liquid phase. Feedstocks used were two hydrocarbon mixtures with different 1-butene/2-butene ratios but the same total amount of n-butenes. The concentrations of the n-butenes are given in Table 2. In addition, the mixtures contain the following components, which add up to 100 wt %:
  isobutane less than 2%
  n-butane more than 21%
  isobutene less than 1%

All of the mixtures therefore contained 1-butene quantities below the 1-butene concentration which comes about in the thermodynamic equilibrium of the n-butenes at reaction temperature (in this case, reactor entry temperature 60° C.), or were free from 1-butene within the bounds of analytical detectability (Example 12).

The catalyst used was the same heterogeneous nickel catalyst as in Examples 1 to 5.

Downstream of each reaction stage, the oligomers were removed from the butanes and unreacted butenes and were analysed for their composition as described in Example 1. A part of the stream containing butanes and unreacted butenes was returned to the preceding reactor (for amounts see Table 2). The part of this mixture not recycled was used as fresh feed for the subsequent reaction stage (where present).

TABLE 2

Analysis of Examples 6 to 11

| Example No. | 6 | 7 | 8 | 9 | 10 | 11 | 12 |
|---|---|---|---|---|---|---|---|
| Fresh feed [g/h] | 850 | 850 | 850 | 850 | 850 | 850 | 850 |
| 1-Butene concentration in fresh feed [wt %] | 0.5 | 0.5 | 0.5 | 4.0 | 4.0 | 4.0 | 0.0 |
| 2-Butene concentration in fresh feed [wt %] | 75.5 | 75.5 | 75.5 | 72.0 | 72.0 | 72.0 | 76.0 |
| Recycle amount [g/h] | | | | | | | |
| 1st stage | 100 | 100 | 100 | 100 | 100 | 100 | 100 |
| 2nd stage | — | 100 | 100 | — | 100 | 100 | 100 |
| 3rd stage | — | — | 100 | — | — | 100 | 100 |
| Entry temperature [° C.] | | | | | | | |
| 1st stage | 60.0 | 60.0 | 60.0 | 60.0 | 60.0 | 60.0 | 60.0 |
| 2nd stage | — | 60.0 | 60.0 | — | 60.0 | 60.0 | 60.0 |
| 3rd stage | — | — | 70.0 | — | — | 70.0 | 70.0 |
| Exit temperature [° C.] | | | | | | | |
| 1st stage | 60.9 | 60.9 | 60.9 | 60.9 | 60.9 | 60.9 | 60.9 |
| 2nd stage | — | 60.6 | 60.6 | — | 60.6 | 60.6 | 60.6 |
| 3rd stage | — | — | 70.4 | — | — | 70.4 | 70.4 |
| Per pass conversion [wt %] | | | | | | | |
| 1st stage | 35.1 | 35.1 | 35.1 | 34.7 | 34.7 | 34.7 | 35.1 |
| 2nd stage | — | 42.5 | 42.5 | — | 42.5 | 42.5 | 42.5 |
| 3rd stage | — | — | 59.2 | — | — | 59.2 | 59.2 |

TABLE 2-continued

Analysis of Examples 6 to 11

| Example No. | 6 | 7 | 8 | 9 | 10 | 11 | 12 |
|---|---|---|---|---|---|---|---|
| Concentration of oligomers in reactor effluent [wt %] | | | | | | | |
| 1st stage | 26.4 | 26.4 | 26.4 | 26.1 | 26.1 | 26.1 | 26.4 |
| 2nd stage | — | 27.2 | 27.2 | — | 27.2 | 27.2 | 27.2 |
| 3rd stage | — | — | 26.9 | — | — | 27.0 | 26.9 |
| Overall conversion [%] | 38.7 | 68.2 | 89.4 | 38.4 | 67.9 | 89.3 | 89.4 |
| $C_8$ selectivity [%] | 84.7 | 83.9 | 82.6 | 84.7 | 83.9 | 82.7 | 82.6 |
| Mass fractions in the hydrogenated $C_8$ mixture [wt %] | | | | | | | |
| n-Octane | 14.4 | 14.7 | 14.5 | 15.2 | 15.1 | 14.8 | 14.5 |
| Methylheptane | 66.6 | 66.8 | 66.3 | 67.8 | 67.5 | 66.9 | 66.2 |
| Dimethylhexane | 18.9 | 18.5 | 19.1 | 17.0 | 17.4 | 18.3 | 19.3 |
| Iso index | 1.045 | 1.039 | 1.047 | 1.019 | 1.024 | 1.035 | 1.049 |

CONCLUSION

The comparison of the non-inventive Examples 1 and 2 shows that the 1-butene content has a perceptible influence on the Iso index of the resulting $C_8$ olefin mixture. Examples 2 to 5 show that the oligomerization process known from the prior art is unsuitable for producing di-butenes that can be used for plasticizer production from $C_4$ streams with a low 1-butene content.

But the comparison of the non-inventive Examples 2 to 5 with the inventive Examples 6 to 12 demonstrates that in accordance with the process of the invention, $C_8$ mixtures with a low Iso index of below 1.05 can be prepared even when the reactant stream employed contains extremely small fractions of 1-butene, or none. The three-stage processes in this case achieve an overall conversion of approximately 90%. The $C_8$ selectivity is slightly above that of the conventional process.

The inventively modified OCTOL process has therefore been set up, by limitation of the conversion in its individual oligomerization steps, in a particular way for the productive utilization of $C_4$ feedstock mixtures having a low 1-butene content, but nevertheless yields a $C_8$ product mixture having an Iso index suitable for the production of plasticizer alcohols.

LIST OF REFERENCE NUMERALS 1 reactant mixture
2 reaction zone
3 oligomerizate
4 distillation column
5 top stream
6 liquid phase stream
7 recycle stream
8 transfer stream
9 assessment boundary
10 overall process (two-stage)
101 first step sequence
102 second step sequence
11 reactant mixture
12 first reaction zone
13 first oligomerizate
14 first distillation column
15 first top stream
16 first liquid phase stream
17 first recycle stream
18 first transfer stream
21 hydrocarbon mixture provided for the second stage
22 second reaction zone
23 second oligomerizate
24 second distillation column
25 second top stream
26 second liquid phase stream
27 second recycle stream
28 second transfer stream
29 fractionation
30 productive utilization
32 third reaction zone
33 third oligomerizate
34 third distillation column
36 combined liquid phase streams/third liquid phase stream
37 $C_8$ column
38 $C_8$ product mixture
39 liquid phase product of the $C_8$ column
40 $C_{12}$ column
41 $C_{12}$ product mixture
42 $C_{12+}$ product mixture

The invention claimed is:

1. A process for preparing a $C_8$ olefin or a $C_{12}$ olefin by oligomerization of butenes, comprising:
   a) oligomerizing a portion of butenes present in a hydrocarbon mixture comprising a 2-butene and a further linear butene other than the 2-butene, to give one or more $C_8$ olefins and to give one or more $C_{12}$ olefins and optionally to give one or more $C_{12+}$ olefins, by contacting of the hydrocarbon mixture with an oligomerization catalyst arranged in a reaction zone, at a reaction temperature prevailing in the reaction zone, to give an oligomerizate comprising the prepared oligomers and one or more unreacted butenes;
   b) removing the unreacted butenes from the oligomerizate; and
   c) optionally, recycling a part of the removed unreacted butenes to the oligomerizing a);

wherein:
   the sequence of a), b) and c) is carried out at least once with inclusion of the recycling c);
   during the first time that the oligomerizing a) is carried out, a concentration of 1-butene in the hydrocarbon mixture, based on the concentration of linear butenes, is less than or equal to an equilibrium concentration of 1-butene, resulting from the reaction temperature of the sequence carried out for the first time, within the fraction of the linear butenes present in the hydrocarbon mixture during the first time;

the $C_8$ olefins are obtained as a $C_8$ product mixture whose Iso index is less than 1.2;

during the sequence carried out for the first time, the conversion of butenes, assessed directly over a first reaction zone, is limited to a first limit value of between 26.1 and 40 wt %; and the limiting of the conversion in the oligomerization is accomplished by limiting the reaction temperature of the oligomerization to a maximum temperature of between 40° C. and 140° C.

2. The process of claim 1, wherein:

the sequence of a), b) and c) is carried out at least two times one after another, and in the second sequence carried out, the conversion of butenes, assessed directly at a second reaction zone, is limited to a second limiting value of between 5 and 50 wt %.

3. The process of claim 2, wherein:

the sequence of a), b) and c) is carried out at least three times one after another, and in the third sequence carried out, the conversion of butenes, assessed directly at a third reaction zone, is limited to a third limiting value of between 5 and 65 wt %.

4. The process of claim 3, wherein:

the sequence of a), b) and c) is carried out at least four times one after another, and in the fourth sequence carried out, the conversion of butenes, assessed directly at a fourth reaction zone, is limited to a fourth limiting value of between 5 and 80 wt %.

5. The process of claim 4, wherein:

the sequence of a), b) and c) is carried out at least five times one after another, and in the fifth sequence carried out, the conversion of butenes, assessed directly at a fifth reaction zone, is limited to a fifth limiting value of between 5 and 95 wt %.

6. The process of claim 1, wherein an overall conversion of butenes achieved after all of the sequences of a), b) and c) have been carried out is between 5 and 100 wt %.

7. The process of claim 1, wherein the limiting of the conversion in the oligomerization is accomplished by limiting the reaction temperature of the oligomerization to a maximum temperature of between 45° C. and 120° C.

8. The process of claim 1, wherein more than 80 wt % of the oligomers prepared are $C_8$ olefins.

9. The process of claim 1, wherein a composition of the $C_8$ olefins obtained is as follows, adding up to 100 wt %:

n-octenes: 10 to 25 wt %;
methylheptenes: 50 to 80 wt %;
dimethylhexenes: 10 to 30 wt %.

10. The process of claim 1, wherein the $C_8$ product mixture has an Iso index of less than 1.1.

11. The process of claim 1, wherein the hydrocarbon mixture in the sequence carried out for the first time is a reactant mixture having the following composition, which adds up to 100 wt %:

1-butene: less than 10 wt %;
2-butenes: 20 to 90 wt %;
isobutene: less than 5 wt %;
n-butane: less than 80 wt %;
isobutane: less than 80 wt %; and
others: less than 5 wt %.

12. The process of claim 1, carried out in a plant within which exactly one reaction zone is assigned to each sequence carried out.

13. The process of claim 1, wherein in each sequence apart from the last sequence, a non-recycled part of the removed unreacted butenes is provided as a hydrocarbon mixture for the subsequent step sequence.

14. The process of claim 13, further comprising:

performing at least one selected from the group consisting of:

(a) totally hydrogenating the non-recycled part of the removed unreacted butenes in the last sequence, to obtain a butane mixture;

(b) oxidatively or non-oxidatively dehydrogenating the non-recycled part of the removed unreacted butenes in the last sequence, to obtain butadiene;

(c) hydroformylating the non-recycled part of the removed unreacted butenes in the last sequence, to obtain pentanals;

(d) oxidizing the non-recycled part of the removed unreacted butenes in the last sequence, to obtain maleic anhydride;

(e) metathesizing the non-recycled part of the removed unreacted butenes in the last sequence;

(f) hydrating the non-recycled part of the removed unreacted butenes in the last sequence, to obtain butanols;

(g) alkylating the non-recycled part of the removed unreacted butenes in the last sequence;

(h) isomerizing the non-recycled part of the removed unreacted butenes in the last sequence;

(i) carbonylating the non-recycled part of the removed unreacted butenes in the last sequence;

(j) cracking the non-recycled part of the removed unreacted butenes in the last sequence in a steamcracker or in a fluid-catalytic cracker, to obtain hydrocarbons having less than four carbon atoms; and (k) combusting the non-recycled part of the removed unreacted butenes in the last sequence to give thermal energy.

15. The process of claim 1, wherein oligomers obtained in individual sequences are combined and then separated into a $C_8$ product mixture, into a $C_{12}$ product mixture and into a $C_{12+}$ product mixture.

* * * * *